United States Patent [19]

Vértesy et al.

[11] Patent Number: 4,618,602

[45] Date of Patent: Oct. 21, 1986

[54] AMINE CONTAINING PSEUDOOLIGOSACCHARIDE, PHARMACEUTICAL COMPOSITION AND METHOD OF USE

[75] Inventors: László Vértesy, Eppstein; Rudolf Bender, Kronberg; Hans-Wolfram Fehlhaber, Idstein, all of Fed. Rep. of Germany

[73] Assignee: Hoechst Aktiengesellschaft, Fed. Rep. of Germany

[21] Appl. No.: 771,638

[22] Filed: Sep. 3, 1985

[30] Foreign Application Priority Data

Sep. 4, 1984 [DE] Fed. Rep. of Germany ....... 3432432

[51] Int. Cl.[4] ...................... A61K 31/73; C08B 37/00
[52] U.S. Cl. ........................................ 514/54; 424/49;
536/18.7; 536/123; 514/866; 514/835
[58] Field of Search ................ 536/18.7; 514/54, 835, 514/866; 424/49

[56] References Cited

U.S. PATENT DOCUMENTS 4,062,950 12/1977 Frommer et al. ................... 536/18.7
4,065,557 12/1977 Frommer et al. ................... 536/18.7
4,254,256 3/1981 Otani et al. ......................... 536/18.7

Primary Examiner—Johnnie R. Brown
Attorney, Agent, or Firm—Finnegan, Henderson, Farabow, Garrett & Dunner

[57] ABSTRACT

Pseudooligosaccharide of the formula I

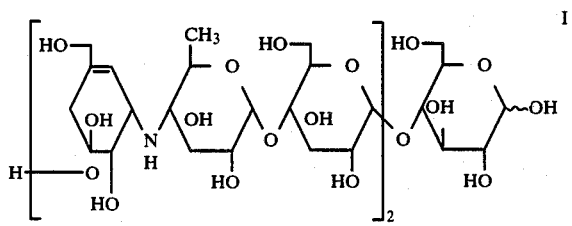

and physiologically acceptable salts thereof with acids, a process for the preparation, pharmaceutical products and the use are described. The compound has a α-glucosidase-inhibiting action.

5 Claims, 1 Drawing Figure

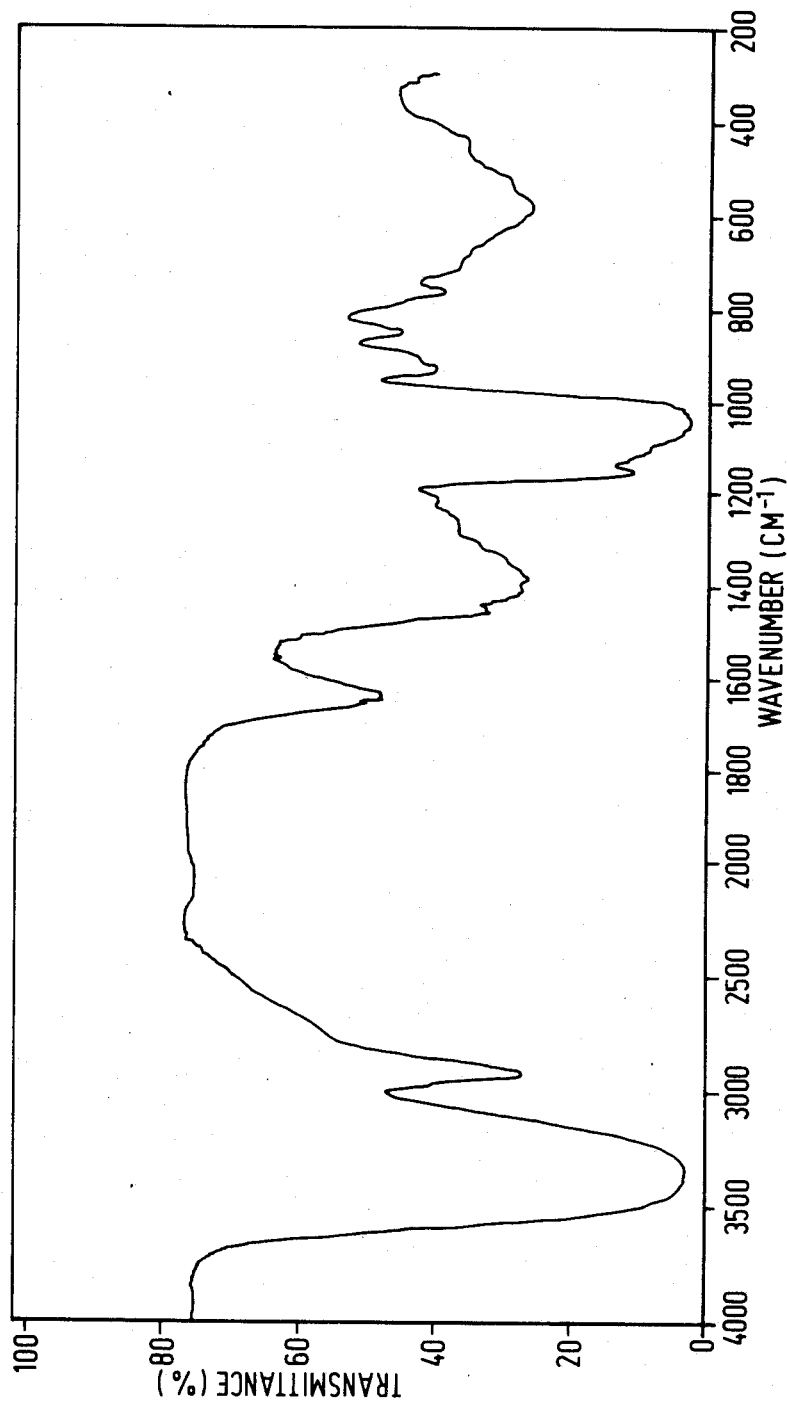

AMINE CONTAINING PSEUDOOLIGOSACCHARIDE, PHARMACEUTICAL COMPOSITION AND METHOD OF USE

The invention relates to a novel biologically active pseudooligosaccharide and its physiologically acceptable salts. It has α-glucosidase-inhibiting properties, i.e., for example, α-amylase- and disaccharidase-inhibiting properties, and can therefore be used in human and veterinary medicine, in animal nutrition and in starch biotechnology.

The pseudooligosaccharide according to the invention has the following formula I

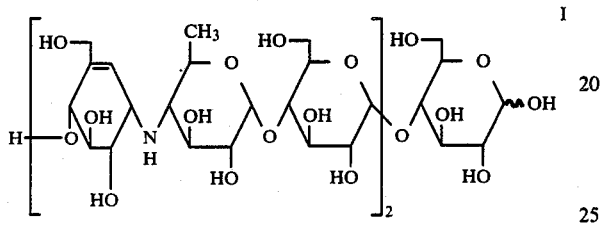

It has a basic character and reducing properties and, in accordance with the empirical composition of $C_{44}H_{74}N_2O_{30}$, a molecular weight of 1,110. This pseudooligosaccharide is also called the inhibitor AI-5662 in the following text. The invention relates to the inhibitor AI-5662 and its physiologically acceptable salts with acids.

The invention furthermore relates to a process for the preparation of the pseudooligosaccharide of the formula I, pharmaceutical products containing a compound of the formula I and the use as a medicament, diagnostic aid and reagent.

The process for the preparation of the pseudooligosaccharide of the formula I comprises culturing, in a fermentation medium by the submerged method, a Streptomycetes which produces the pseudooligosaccharide of the formula I, isolating the inhibitor from the mycelium or the culture filtrate in a manner which is known per se and purifying it. Of the Streptomycetes, Streptomyces nov. spec. FH 1717 is suitable. This strain has been deposited in the Deutsche Sammlung von Mikroorganismen (DSM) (German Collection of Microorganisms) under the registration No. DSM 3006. The variants and mutants of this strain, however, can also be used to obtain the inhibitor AI-5662.

The taxonomic properties of Streptomyces FH 1717, DSM 3006, cannot be matched with any description of a Streptomycetes according to Bergey's Manual of Determinative Bacteriology, 8th edition. publisher: Williams & Wilkins Corp. Baltimore, 1974 or other descriptions known from the literature. Differences from the strains described exist in essential physiological features. The following Table 1 shows morphological criteria and results of physiological investigations.

TABLE 1

| Identification of the Streptomyces novo species FH 1717 | |
| --- | --- |
| Aerial mycelium color identified as | gray Streptomyces species |
| Substrate mycelium color | |
| Endopigment | black |
| Exopigment | dark |
| Morphology of the spore chain | RA/S |
| Spore surface | smooth |
| Melanin formation | |
| Complex | + |
| Synthetic | + |
| C sources utilization spectrum | |
| Glucose | + |
| Arabinose | + |
| Xylose | + |
| Fructose | (+) |
| Rhamnose | + |
| Lactose | − |
| Sucrose | (+) |
| Raffinose | (1) |
| Mannitol | 1 |
| Inositol | − |
| Acid series | |
| Gluconate | + |
| Citrate | − |
| Malonate | − |
| Malate | + |
| Lactate | + |
| Oxalate | + |
| Acid formation | − |
| Utilization of macromolecules | |
| Gelatine | + |
| Hemolysis | −/− |
| Egg yolk reaction | |
| Lecithovitellin reaction | − |
| Pearly layer | 5 |
| Proteolysis | 7 |
| Urea cleavage | + |
| Nitrate 1 g | + |
| Nitrite 1 g | + |
| Nitrite 3 g | − |
| Lysozyme (μg/ml) | |
| 0 | + |
| 10 | − |
| 50 | − |
| 100 | − |
| Allantoin degradation | 1 |
| Esculin cleavage | + |
| Hippuric acid cleavage | (+) |
| Voges-Proskauer reaction | 1 |
| NaCl resistance (%) | |
| 4 | + |
| 7 | − |
| 10 | − |
| 13 | − |
| Antibiotic activity (inhibition in mm) | |
| Escherichia coli DSM 682 | − |
| Pseudomonas aeruginosa DSM 50 071 | − |
| Corynebacterium bovis | − |
| Staphylococcus aureus DSM 346 | − |
| Bacillus cereus DSM 486 | − |
| Mucor ramannianis NRRL 1839 | − |
| Candida albicans NRRL Y-477 | − |
| Temperature range | |
| 20 | + |
| 28 | + |
| 37 | + |
| 45 | 7 colonies |
| 55 | − |

+ growth or positive reaction,
(+) slight growth,
1 very slight growth,
− negative reaction.

Streptomyces species as shown in Table 1 have not yet been described in the literature. Streptomyces FH 1717 is consequently novel. The invention therefore also relates to the Streptomyces novo species FH 1717, DSM 3006.

The inhibitor AI-5662 is advantageously obtained by the following procedure:

Streptomycesnovo spec. FH 1717 is cultured in an aqueous nutrient medium under submerged and preferably aerobic conditions until an adequate concentration of the inhibitor AI-5662 is obtained. The nutrient medium contains on the one hand sources of carbon, such as, for example, carbohydrates, and on the other hand nutrient salts and sources of nitrogen, suitable nitrogen compounds including, for example, protein-containing materials. Preferred compounds which supply carbon are glucose, sucrose, glycerol, malt extract, starch, oils, fats and the like. Preferred substances which supply nitrogen are, for example, cornsteep liquor, yeast extracts, soybean flour, fish meal, skim milk powder, partly digested casein or meat extract. So-called "synthetic" nutrient solutions can also be used. It may furthermore be beneficial to add trace elements, such as, for example, zinc, magnesium, iron, cobalt or manganese, to the fermentation medium.

The fermentation which leads to the formation of the inhibitor AI-5662 can be carried out within a wide temperature range. For example, it is carried out at temperatures between 10° and 40° C., preferably between approximately 20° and 35° C. The pH of the medium is likewise kept at values which are favorable to the growth of the microorganisms, for example at a pH between 4.0 and 10.0, preferably between 6.0 and 9.5. Depending on the nutrient medium, such as, for example, its qualitative and quantitative composition, and the fermentation conditions, such as, for example, the rate of aeration, temperature or pH, the AI-5662 is usually formed in the culture solution after about 1–10 days.

The inhibitor AI-5662 is found both in the mycelium and in the culture filtrate from the fermentation. Most of the AI-5662 is generally to be found in the culture filtrate. The aqueous phase is therefore advantageously separated off from the mycelium, for example by filtration or centrifugation, and the pseudooligosaccharide is isolated from the particular phases by processes which are known per se and purified. A large number of processes are suitable for this, such as, for example, chromatography on inorganic carriers, such as $Al_2O_3$ or silica gel, and separation on ion exchangers, molecular sieves or adsorption resins, solvent or salt precipitations, ultrafiltration, Craig partition and the like.

A preferred process for obtaining the AI-5662 comprises adsorbing the inhibitor from the culture filtrate onto a suitable resin, for example based on polystyrene, separating off this laden resin and isolating the inhibitor AI-5662 by elution with suitable buffer solutions, such as, for example, phosphate or Na acetate buffer solution, or with organic solvents, if appropriate containing water, such as, for example, methanol, ethanol, acetone or, preferably, aqueous isopropanol. The inhibitor-containing eluates are concentrated by ultrafiltration in a known manner, demineralization simultaneously being carried out. The ion-deficient aqueous solution of the AI-5662 is then separated by chromatography on an ion exchanger column in a manner which is known per se. Strongly or weakly acid cation exchangers, for example based on styrene/divinylbenzene copolymers, which carry —$SO_3H$ or —COOH groups as functional groups (®Dowex 50 or ®Amberlite CG 120) or based on modified sulfopropyl-cellulose (SP- ®Sephadex), are preferably used as the ion exchangers, but a large number of other commercially available cation exchangers can also be used. The next step in the purification is the use of a molecular sieve, such as, for example, based on polyacrylamide gel (®Biogel P-6) or based on modified cellulose (®Sephadex G-25). The α-amylase inhibitor AI-5662 is obtained by collecting the molecular weight range around 1,100 Da. However, the substance obtained by the process mentioned may still contain small amounts of impurities. In such cases, it is beneficial to carry out a further separation on silica gel as subsequent purification. A mixture of n-propanol/ethyl acetate/water/glacial acetic acid in the proportions 6:1:3:0.5 is advantageously used as the eluting agent. The inhibitor-containing eluates are combined, concentrated in vacuo and freeze-dried. The specific activity of such a product is $4 \times 10^4$ α-amylase inhibitor units per mg.

The pure inhibitor AI-5662 is a colorless, amorphous pseudooligosaccharide. It contains nitrogen and has a weakly basic character. Thus, in high voltage electrophoresis in acid buffers, such as, for example, aqueous formic acid/acetic acid mixtures, the inhibitor AI-5662 migrates as the cation in the direction of the cathode. The substance according to the invention contains glucose in bonded form: acid hydrolysis of the substance gives glucose, alongside other, usually nitrogen-containing, cleavage products. A further characteristic of the inhibitor AI-5662 is that it has reducing properties which, as is customary in sugar chemistry, can be demonstrated with, for example, triphenyltetrazoliumchloride (TTC). The compound according to the invention has the abovementioned formula. The substance is readily soluble in water. The absorption spectrum of ultraviolet light, measured from 400 to 210 nm in aqueous solution, shows an end absorption at the low wavelength. The infrared spectrum (recorded in KBr) is shown in the figure.

Several α-glucosidase inhibitors with pseudooligosaccharide character have already been described in the literature: E. Truscheit et al., Angew. Chem. 93, pages 738–755 (1981), T. Tajiri et al., Agric. Biol. Chem. 47, pages 671–679 (1983), K. Yokose et al., J. Antibiotics, 36, pages 1157–1175 (1983).

The inhibitor according to the invention differs from all the known α-glucosidase inhibitors by its structural formula I and also in some cases by the reducing properties, and this is therefore a novel substance which can be obtained microbiologically in good yields.

The α-amylase- and disaccharidase-inhibiting properties of the inhibitor AI-5662 according to the invention are of interest in respect of use as a therapeutic against diabetes and prediabetes as well as adiposity and to supplement the diet. On the basis of its properties, it is also useful as a reagent for diagnostic purposes.

Starch-containing foodstuffs and luxury foods lead to an increase in the blood sugar and thereby also to an increased secretion of insulin by the pancreas in animals and humans.

Hyperglycemia occurs due to breaking up of the starch in the digestive tract to give glucose, under the influence of amylase and maltase.

In diabetics, the hyperglycemia is particularly pronounced and long-lasting.

Both alimentary hyperglycemia and hyperinsulinemia following starch intake can be reduced by the α-glucosidase inhibitor AI-5662 according to the invention. This effect is dose-dependent. The amylase inhibitor according to the invention can therefore be employed as a therapeutic in cases of diabetes, prediabetes and adiposity and to supplement the diet. For this purpose, oral administration, in particular at mealtimes, is recommended. The dosage should depend on the weight of the patient and the individual requirement and is about 5-300 mg per dose, advantageously taken at each mealtime. However, in individual justified cases, the dosage can also be above or below this value.

The α-glucosidase inhibitor according to the invention is particularly suitable for ora administration. It can be administered as the pure substance, as a physiologically acceptable salt with acids or in the form of a pharmaceutical formulation, using the customary auxiliaries and excipients. Combined use with other medicaments, such as hypoglycemic or lipid-lowering substances, may also be advantageous. Since high molecular weight saccharides are not, or not noticeably, absorbed as such from the digestive tract, no toxicologically unacceptable side effects are to be expected of the substance according to the invention. Accordingly, no notworthy signs were detected following oral administration even of high doses of the α-glucosidase inhibitor AI-5662 to experimental animals. To test the pharmacological action of the AI-5662, fasting male Wistar rats weighing between 200 and 250 g were given an oral administration of the inhbitor AI-5662 according to the invention simultaneously with 2 g of starch per kg of body weight. The efficacy of the product was demonstrated by determining the blood sugar concentrations in blood samples taken before, during and after administration of the α-amylase inhibitor. Besides blood glucose regulation, the polypeptides according to the invention can also be used for inhibiting salivary α-amylase. This enzyme effects digestion of starch in the mouth, and the sugar thus formed promotes caries of the teeth. The compound according to the invention can therefore be used to prevent or reduce the development of caries.

It can furthermore be used as a biochemical reagent and as a diagnostic agent.

Amylase test

One amylase inhibitor unit (AIU) is defined as the amount of inhibitor which is capable of inhibiting two amylase units (AU) to the extent of 50% under the test conditions. By international agreement, one amylase unit is the amount of enzyme which cleaves 1 μEq of glucosidic bonds in starch in one minute. The μ equivalents of glucosidic bonds cleaved are determined photometrically, with dinitrosalicylic acid, as μEq of reducing sugars. The data are calculated as μmol of maltose, determined with the aid of a maltose calibration line.

The tests are carried out as follows:

α-Amylase from the pancreas of pigs and the solutions to be tested are preincubated together in 1.0 ml of 20 mM phosphate buffer, pH 6.9, +10 mM NaCl at 37° C. for 10-20 minutes. The enzymatic reaction is started by addition of 1.0 ml of soluble starch (0.25% strength in the buffer described) according to Zulkowski. After exactly 10 minutes, the reaction istopped with 2.0 ml of dinitrosalicylic acid color reagent (from Boehringer Mannheim: Biochemica-Information II), and the mixture is heated in a boiling waterbath for 5 minutes for color development. After cooling, the extinction is measured against the reagent blank at 546 nm. The 50% inhibition is determined graphically by means of a probability plot in comparison with the non-inhibited enzyme reaction using various amounts of inhibitor.

EXAMPLE 1

To obtain AI-5662, the inoculum was cultured (culture of the microorganism)—as is customary in microbiological practice—from a freeze-dried permanent form of the organism Streptomyces novo species FH 1717, DSM 3006, via individual colony passage and using slant tubes. The mass production of spores necessry for fermentation was likewise carried out on a solid nutrient medium in Roux bottles.

Agar medium for the plate, slant tube and Roux bottle 40 g of crushed oats were finely ground, 950 ml of tapwater were added and the mixture was homogenized with an Ultra-Turrax for 5 minutes. 18 g of agar were then added and the mixture was sterilized at 120° C. for 20 minutes.

The inoculated tube and the Roux bottle were incubated at 28° C. for 5 days and then kept at +4° C. The spores were flushed from the solid nutrient medium with 10 ml of sterilized distilled water or physiological saline solution. 5 ml of the suspension were used to inoculate a 2,000 ml conical flask which had been charged with 500 ml of sterilized aqueous nutrient solution with a pH of 7.3 and with the following composition (data in % by weight)

1.00% of glucose 0.40% of casein peptone 0.40% of meat extract 0.25% of NaCl 0.05% of yeast extract 0.05% of liver powder.

The flask was shaken on a shaking machine at 220 rpm at +28° C. for 24 hours. Thereafter, this preculture was transferred into a 12 liter Braun fermenter which had been charged with 9 liters of sterilized aqueous nutrient solution and in which the pH was 7.4. The composition of the nutrient solution for the main culture was as follows (data in % by weight).

2.0% of meat extract 2.0% of malt extract 1.0% of calcium carbonate 0.1% of antifoam agent to 100% with water.

The main culture was stired at 500 rpm at 28° C. for 4 days, the air supply being 120 liters per hour. The content of α-glucosidase inhibitor was determined in accordance with the instructions of R. Bender et al., Anal. Biochem., 137, 307–312 (1984) after 24, 48, 60, 72, 84 and 96 hours. Under the experimental and culture conditions described, the strain Str. nov. spec. FH 1717 gave on average $3 \times 10^3$ AIU/ml, at a final pH of 8.8.

EXAMPLE 2

8 liters of fermentation solution according to Example 1 were freed from the cell mass with the aid of a centrifuge and the clear liquid phase was brought to pH 9.5. The solution was then introduced onto a column containing 0.8 liters of polystyrene adsorption resin (Diaion ® HP-20) and the column was rinsed with 1.5 liters of water and eluted with water to which increasing amounts of isopropanol had been added. The miure containing 5% of isopropanol detached the inhibitor AI-5662 from the column. These active eluates (1.5 liters) were concentrated by ultrafiltration and demineralized, with addition of water and with further ultrafiltration, until the retained material no longer contained detectable salts. The resulting concentrate (0.2 liter) was separated on sulfopropyl-modified cellulose (SP-Sephadex ®), which had been converted into the acid form ($H^+$ form). The fractions containing the α-amylase-inhibiting activity were eluted by applying an ammonium acetate gradient, pH 5 (0-1 molar). The corresponding fractions were concentrated in ultrafiltration cells (®Amicon) and demineralized. The freeze-dried, active substance was then introduced onto a column (3×35 cm) filled with silica gel and eluted with a mixture of n-propanol/ethyl acetate/water/glacial acetic acid (6:1:3:0.5) by applying pressure. The active eluate was freed from the solvent in vacuo and then taken up in water, the pH was brought to 9 and the mixture was subjected to final purification on Biogel P-6. The column mobile phase here was pure water. The active material obtained was freeze-dried: 0.8 g of a white amorphous powder with an α-amylase-inhibiting action of $4 \times 10^4$ AIU per mg results. The IR spectrum in KBr of this AI-5662 is shown in the figure. Elemental analysis showed 47.6% of carbon, 6.7% of hydrogen, 2.5% of nitrogen and 43.2% of oxygen.

EXAMPLE 3

200 mg of the inhibitor obtained according to Example 2 were dissolved in 1 ml of water and the pH was brought to 2 with sulfuric acid in an ice-bath. The solution was then made up to 10 ml with acetone and left to stand for 30 minutes and the precipitate formed was collected by filtration. The precipitate was dissolved in water and then freeze-dried to give 204 mg of AI-5662 sulfate.

We claim:

1. The pseudooligosaccharide of the formula I

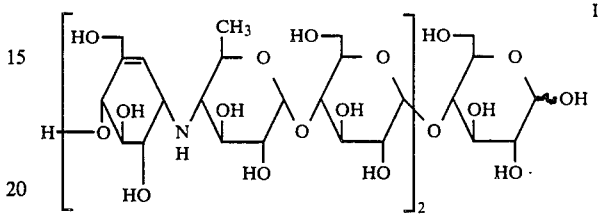

and a physiologically acceptable salt thereof with an acid.

2. A pharmaceutical product for the treatment of diabetes, prediabetes and adiposity containing an effective amount of a pseudooligosaccharide as claimed in claim 1, and a pharmaceutically acceptable carrier.

3. A method which comprises using a pseudooligosaccharide as claimed in claim 1 or a physiologically acceptable salt thereof for inhibition of α-glucosidase.

4. A method which comprises using a compound as claimed in claim 1 for the treatment of diabetes, prediabetes and adiposity.

5. A method which comprises using a compound as claimed in claim 1 as a diagnostic aid, reagent of prophylactic against caries.

* * * * *